(12) United States Patent
Strano et al.

(10) Patent No.: US 10,646,303 B1
(45) Date of Patent: May 12, 2020

(54) METHOD AND APPARATUS FOR DELINEATING THE POSITION OF A SPECIFIC TISSUE

(71) Applicants: Shalom David Strano, Jerusalem (IL); Avraham Suhami, Petah Tikva (IL)

(72) Inventors: Shalom David Strano, Jerusalem (IL); Avraham Suhami, Petah Tikva (IL)

(73) Assignees: S. D. Strano, Jerusalem (IL); A. Sahami, Petach Tikva (IL)

(*) Notice: Subject to any disclaimer, the term of this patent is extended or adjusted under 35 U.S.C. 154(b) by 69 days.

(21) Appl. No.: 15/424,789

(22) Filed: Feb. 4, 2017

(51) Int. Cl.
| | | |
|---|---|---|
| *A61B 90/00* | (2016.01) | |
| *A61B 5/00* | (2006.01) | |
| *G06T 7/00* | (2017.01) | |

(52) U.S. Cl.
CPC ............ *A61B 90/39* (2016.02); *A61B 5/0037* (2013.01); *A61B 2090/397* (2016.02); *A61B 2090/3908* (2016.02); *A61B 2090/3925* (2016.02); *A61B 2090/3958* (2016.02); *A61B 2090/3987* (2016.02); *A61B 2090/3991* (2016.02); *A61B 2090/3995* (2016.02); *G06T 7/0012* (2013.01); *G06T 2207/30096* (2013.01)

(58) Field of Classification Search
CPC .................. A61B 90/39; A61B 5/0037; A61B 2090/3991; A61B 2090/3908; A61B 2090/3958; A61B 2090/3995; A61B 2090/3987; A61B 2090/397; A61B 2090/3925; G06T 7/0012; G06T 2207/30096

See application file for complete search history.

(56) References Cited

U.S. PATENT DOCUMENTS

| 4,811,030 A | * | 3/1989 | Pedersen | G01V 15/00 343/788 |
|---|---|---|---|---|
| 2006/0100509 A1 | * | 5/2006 | Wright | A61N 5/1049 600/426 |
| 2008/0121242 A1 | * | 5/2008 | Revie | A61B 90/39 128/899 |
| 2008/0132800 A1 | * | 6/2008 | Hettrick | A61B 5/0031 600/509 |
| 2011/0004276 A1 | * | 1/2011 | Blair | A61B 5/0002 607/60 |
| 2014/0309522 A1 | * | 10/2014 | Fullerton | A61B 5/0507 600/424 |
| 2017/0038442 A1 | * | 2/2017 | Thonre | A61B 5/055 |
| 2017/0095315 A1 | * | 4/2017 | van der Weide | A61B 90/39 |

* cited by examiner

*Primary Examiner* — Catherine M Voorhees

(57) ABSTRACT

The invention describes the structure and use of passive Markers to indicate the position of suspicious lesions in tissue and a method to mark the lesions and margins of said suspicious lesions that facilitates the communication between the pathologist and the surgeon in order to excise the minimal amount of tissue from the diseased organ.

8 Claims, 8 Drawing Sheets

Fig. 1
Fig. 1A
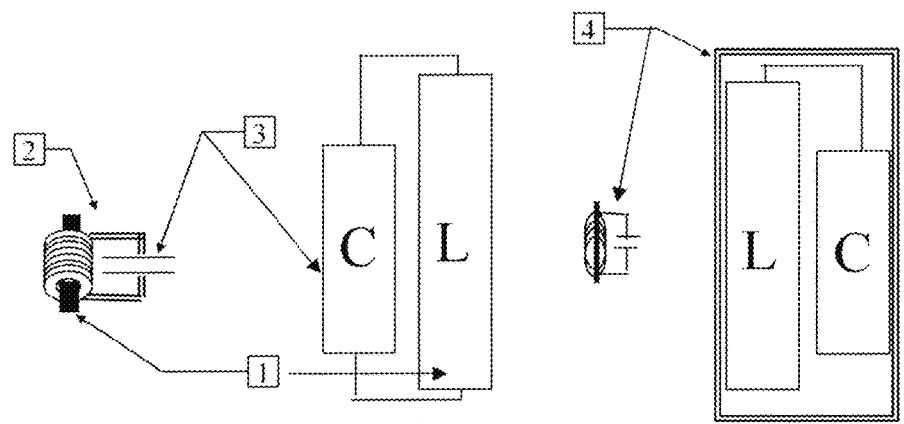
Fig. 1B
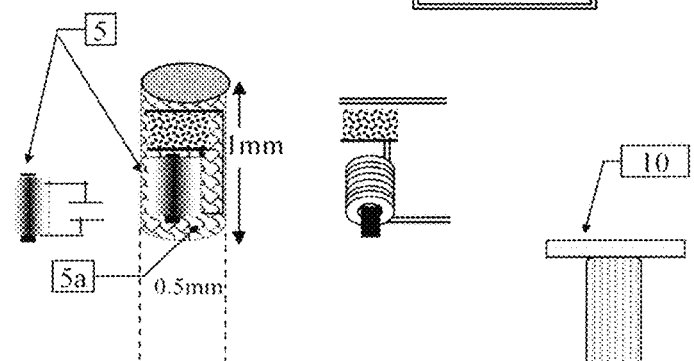
Fig. 1C
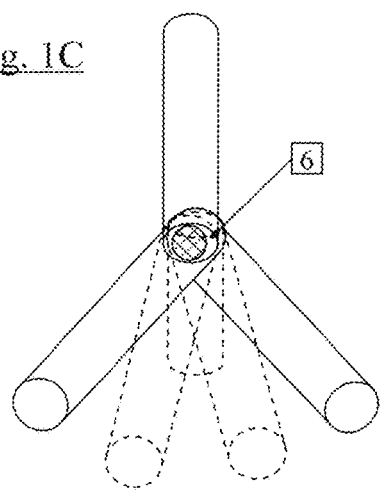
3-Marker
Fig. 1D
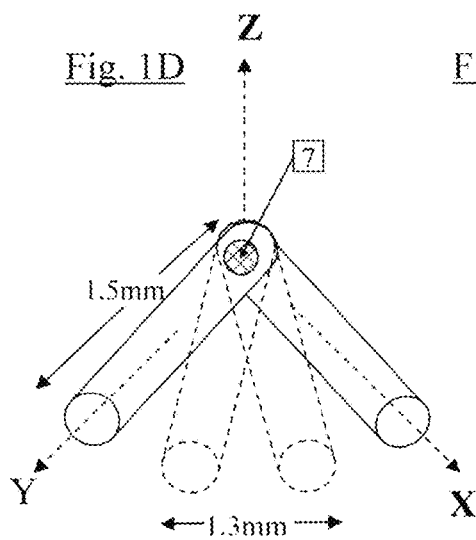
2-Marker
Fig. 1E
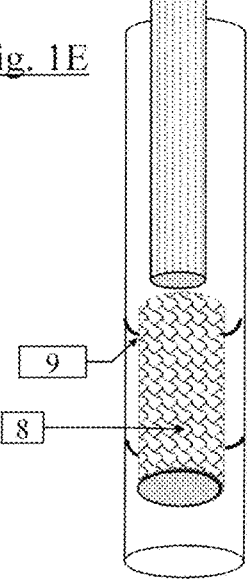
Marker
Copyright ©, all rights reserved ® Avraham Suhami 2015

Fig. 2
Fig. 2A
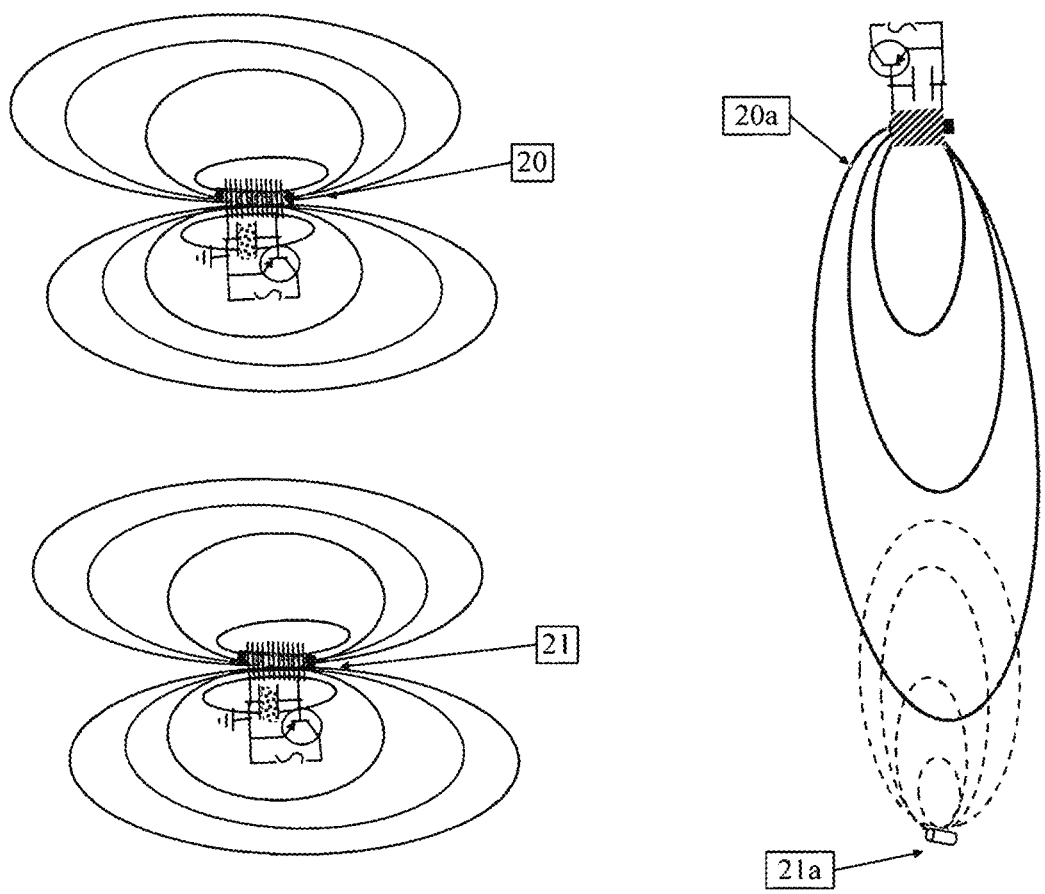
Fig. 2B
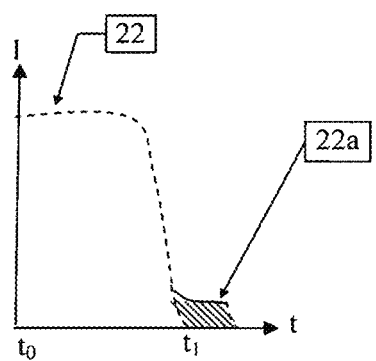
Copyright ©, all rights reserved ® Avraham Suhami 2015

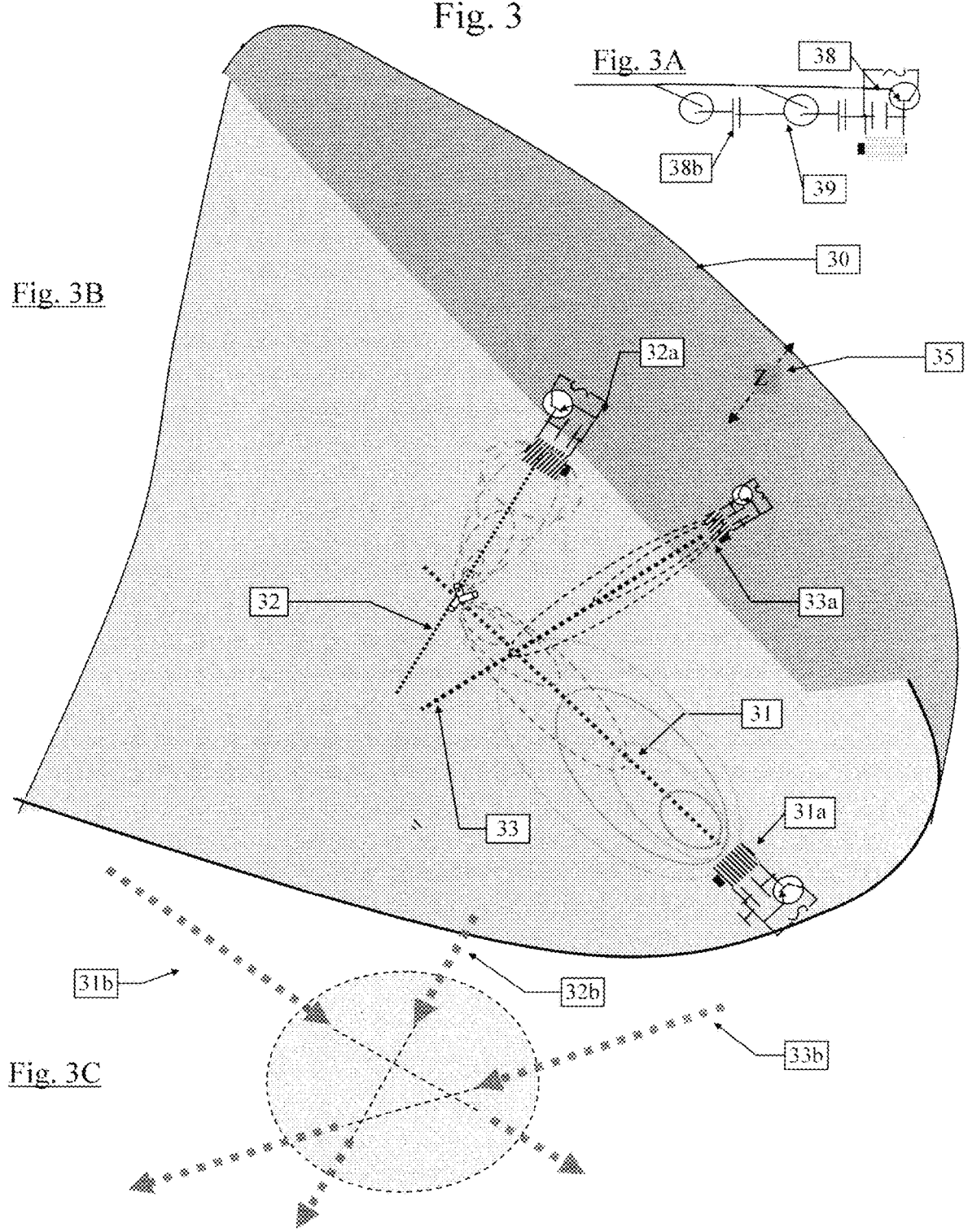

Fig. 5
Fig. 5A
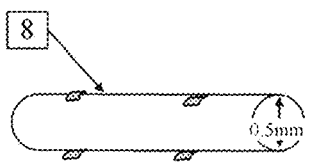
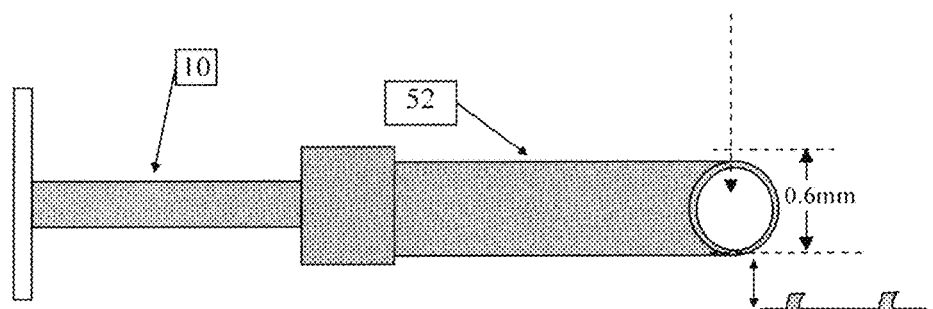
Fig. 5B
Fig. 5C
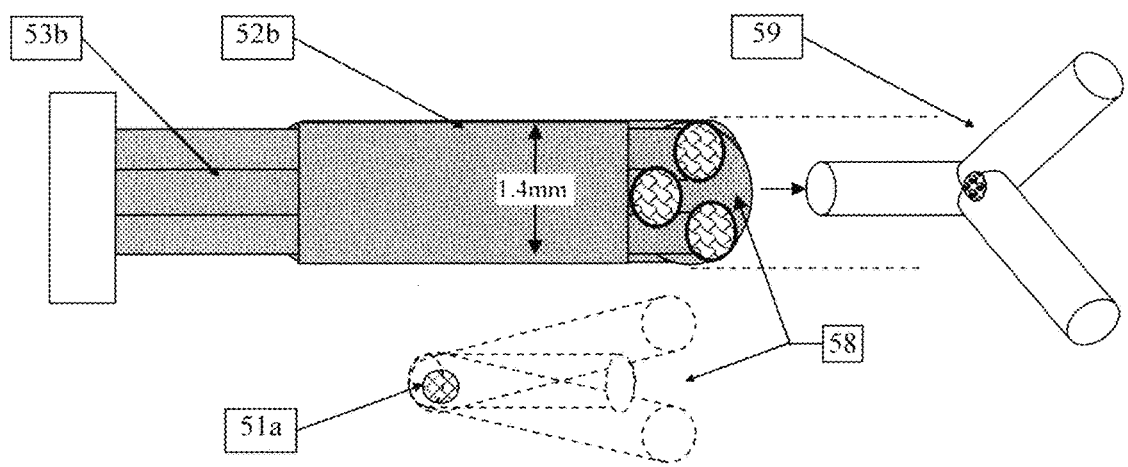
Copyright ©, all rights reserved ® Avraham Suhami 2015

Copyright ©, all rights reserved ® Avraham Suhami 2015

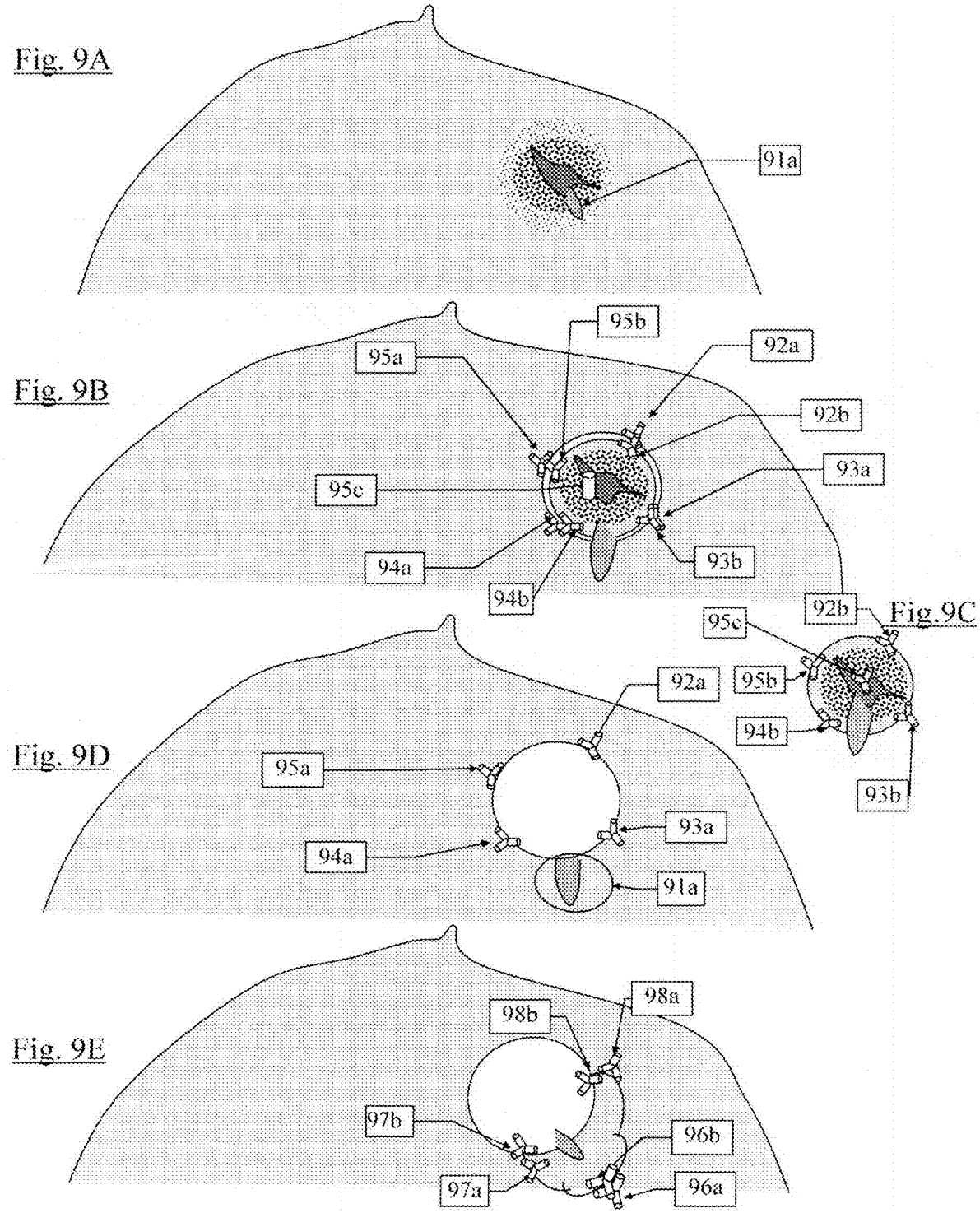

METHOD AND APPARATUS FOR DELINEATING THE POSITION OF A SPECIFIC TISSUE

A portion of the disclosure of this patent document contains material which is subject to (copyright or mask work) protection. The (copyright or mask work) owner has no objection to the facsimile reproduction by anyone of the patent document or the patent disclosure, as it appears in the Patent and Trademark Office patent file or records, but otherwise reserves all (copyright or mask work) rights whatsoever.

FIELD OF THE INVENTION

This invention relates to the field of marking positions of body structures in-vivo accurately, in order to facilitate further diagnostic or surgical procedures.

BACKGROUND OF THE INVENTION

After imaging, of a body tissue, whether by a mammography, ultrasound or MRI Imaging system, by CT or other imaging system, there is a need to mark the position(s) of suspected tumors, lesions or other regions of interest in order to physically convey to the following medical body and/or person the places that may need further examinations using other imaging modalities, surgery or other intervention. In such instances, the physical marking of the location of interest is the minimal information that has to be specified, although additional information related to the patient or the procedure may be encoded on the marker, digitally or in other forms.

The marker may physically mark the position for surgery of a non-palpable breast tumor, any other image detected lesion elsewhere in the body, or of place of irradiation by an electron or proton accelerator or the location of a foreign body or device or part thereof within the body by being attached to such items or site of lesion requiring follow up surveillance.

As the region of the marker may move within the body from the time of first diagnosis to the following stage, it is important both to secure the marker to the body tissue and be able confirm its accurate position with other modalities such as X-ray, ultrasound or MRI.

SUMMARY OF THE INVENTION

Contrary to other markers in use in the industry, our marker is built of passive electronic components that serve to indicate only the position of the marker, in response to an interrogating microwave beam. The values and specific structure of its specific passive components determine the response to a scanning microwave beam generated by the external "Reader" that can calculate its position in space. The marker is inserted by an "applicator", and can be "anchored" in place; it can also be retrieved by the same applicator that after "pulling" its anchors, can retrieve the marker. The marker can be imaged by X-rays. Ultrasound and MRI. There are 3 models of markers, named as "1-Marker", "2-Marker" and "3-Marker" describing the number of non-co-directional LC circuits embedded in them. The position in space of a Marker is defined as the intersection point of the independent LC circuits, in space; in the case of a single LC circuit its position in space is defined as the coordinates of its middle point.

BRIEF DESCRIPTION OF THE DRAWINGS

FIG. 1 (FIGS. 1A-1E) illustrates the 3 possible structures of the Marker that have different specifications although they are all built of inductors and capacitors tucked into tubes of minimal dimensions.

FIG. 2 illustrates the relative positioning of the Marker and the search LC (the Reader) in order to find the Marker's direction, relative to that of the Reader (FIG. 2A) and radiation of the LC circuit (FIG. 2B).

FIG. 3 illustrates the search strategy of the handheld one LC circuit Reader (shown in FIG. 3A), in order to determine the position of a 3-Marker (FIGS. 3B-3C).

FIG. 5 illustrates the basic structure of the "applicator" for inserting the one tube Marker (FIG. 5A), the 2-Marker (FIG. 5B) and the 3-Marker (FIG. 5C) and the way to "anchor" it in the tissue.

FIG. 9 illustrates a method to mark the borders of a biopsy specimen and surgical margins in the breast (FIGS. 9A-9B), in order to minimize the amount of breast tissue excised (FIG. 9C), and to enable further tissue excision if necessary (FIGS. 9D-9E).

DETAILED DESCRIPTION OF THE INVENTION

FIG. 1 illustrates a passive electronic Marker for indicating the position of a lesion or a tumor observed on a mammogram or other imaging modality identifying an area of concern in any part of the body requiring surgical excision or surveillance, for bringing the exact position of said lesion to the attention of a physician, radiologist, an ultrasound specialist or to the surgeon who might operate and excise it. Knowing the exact position of the tumor is of cardinal importance for excising the exact diseased tissue, not too little nor too much. It is thus important to have the marker as small as possible, to only indicate its position. While some alternate designs have opted to inscribe on the Marker, data that convey details relevant to the procedure, our position is to "relay" to the outside world only a "number"; any additional information related to this number" may be entered on a secure electronic file managed by the physician in charge and retrieved by whomever is authorized to do so.

Figure 4:
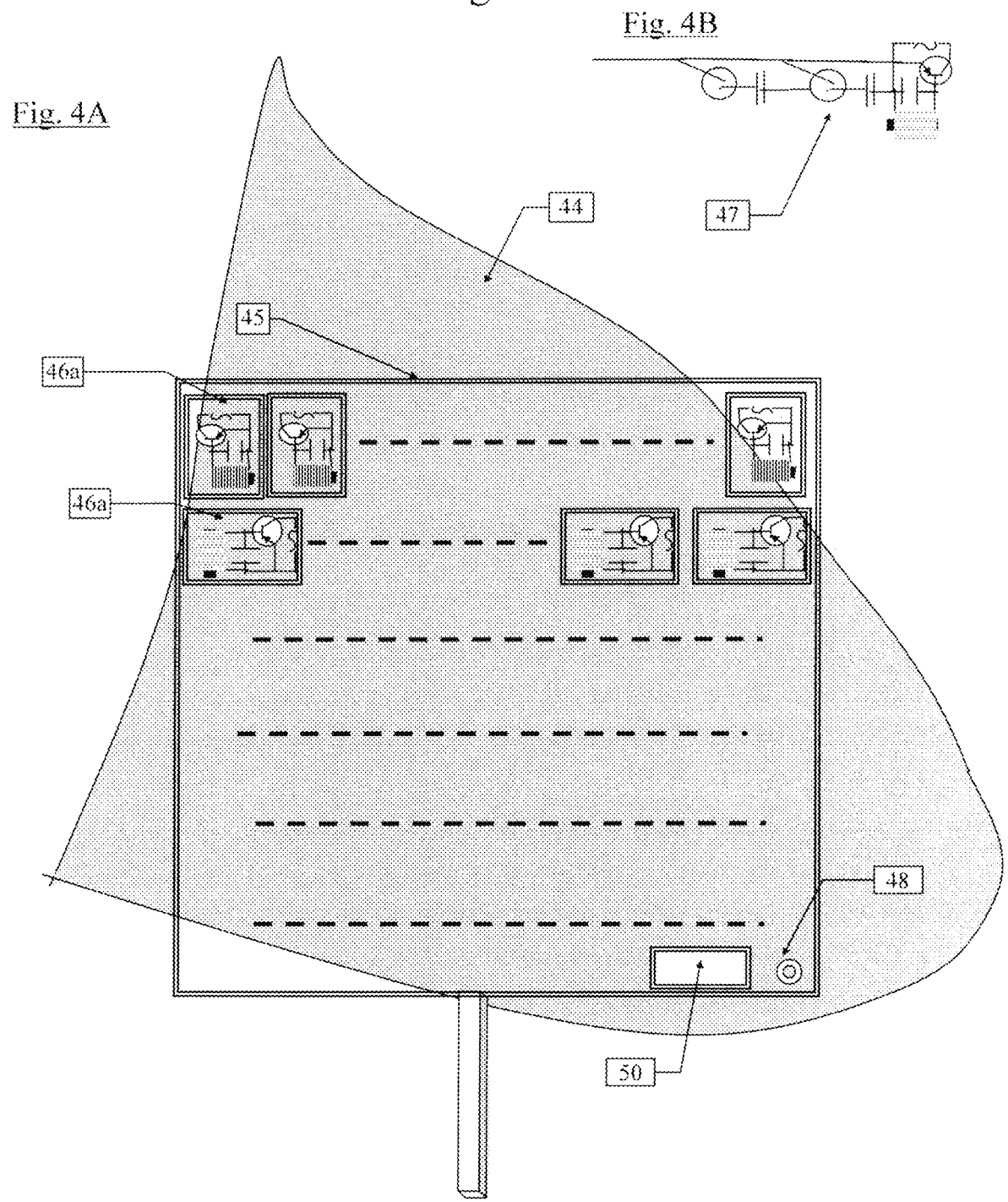
FIG. 4 illustrates a flat hand placed multiple marker position identifier Reader that automates and stores the ongoing search process, displaying on a screen the depth and sound signal amplitude of the underlying marker or markers (FIG. 4A), and changes the value of the capacitance of the marker or markers (FIG. 4B).

Our numbering system is determined by the frequency of the electromagnetic signal that the Marker LC circuit emits and which an outsider uses to access the Marker. Our Marker is extremely simple and includes only passive components (FIG. 1A, 1, 2, 3); in fact only capacitors (FIG. 1A, 3) and inductors (FIG. 1A, 1) of minimal resistance that together form a resonant circuit $f=1/2\pi(LC)^{1/2}$, (FIG. 1A, 2). Our inductance is a wire wound on a tiny ferrite rod (FIG. 1B, 5), or ferrite film, or even a high inductance crystal. The resonant LC circuit magnetic radiation is along the ferrite direction and parallel to the wire-wound on the ferrite. The passive electronic components of the Marker are placed within a receptacle (FIG. 1B, 5a) comprising a thin wall of plastic and or silicone or glass, the receptacle being air filled. The Marker is implantable, its embedded capacitor having a very high dielectric constant and being in the form of a dielectric resonant antenna. Every LC circuit, electrical or mechanical, has a resonant frequency at which it absorbs and radiates energy with maximal efficiency. Non-resonant LC circuits (FIG. 2A, 20, 21) may also transfer energy, but with much less efficiency. Resonant LC circuits at the same resonant frequency 20a, 21a will transfer energy from one circuit to another through magnetic coupling and will vibrate in tandem at the same frequency and phase. Thus a powerful Reader LC circuit (FIG. 1A, 4) scanning the vicinity of a "dormant" LC and aware of the Marker circuit 21a and its resonant frequency, will transfer to it energy by magnetic coupling and cause it to start radiating at the same frequency and phase, after its capacitor is fully charged.

To increase the ability of the inductor coil to absorb energy from the reader, the resistance of the coil is reduced using high conductance materials such as silver, hafnium or graphene.

If the transmitting LC circuit 20a will stop radiating, the recipient LC circuit, the Marker, will drop its initial radiation (FIG. 2b, 22) but still radiate 22a for some time, for as long as its capacitor is still loaded; this emission will be received by the resonant circuit 20a for some time. This residual signal received by the resonant circuit 20a is a proof that the Marker 21a is in the direction of the searching LC circuit 20a.

Figure 6:
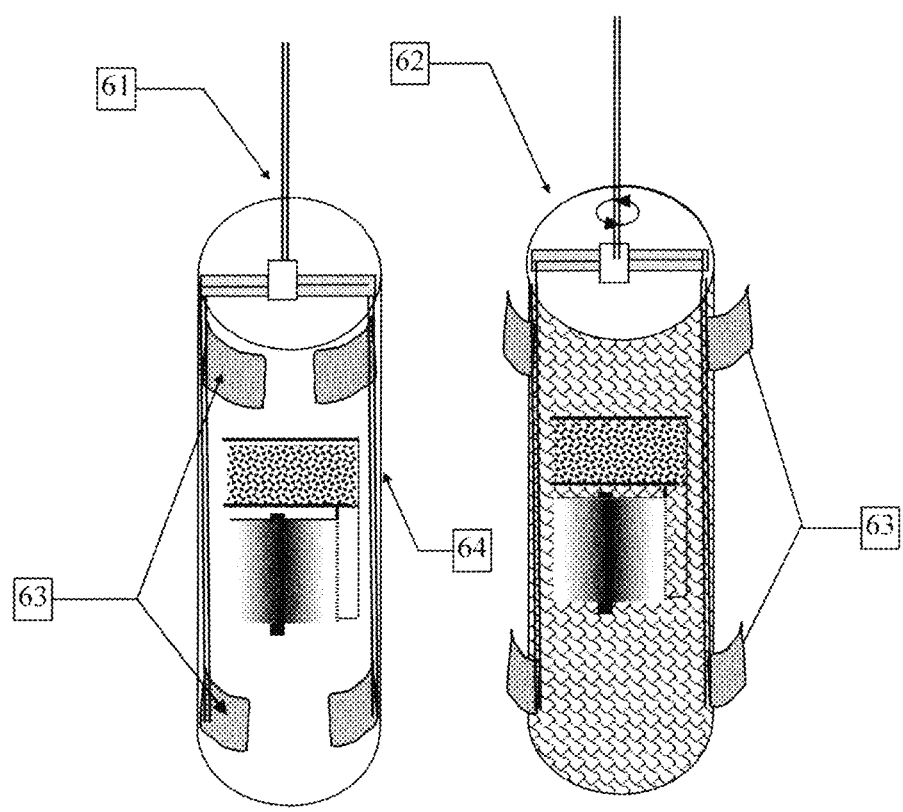
FIG. 6 illustrates the structure of the "Marker tube" with the ability to "spread" anchors by turning a mechanical "lever" on, or retrieve said anchors by turning the mechanical levers in the opposite direction.

As our marker system consist of one, two or three LC resonant circuits we shall refer to a single LC circuit embedded in a tube (FIG. 1B, 5a) as a Marker, to a two tube circuit as a 2-Marker (FIG. 1D, 7), and to a 3 tube circuit as a 3-Marker (FIG. 1C, 6).

The response of a Marker to a "search" signal of the Reader is a function among other factors, of the cumulative energy stored in the Capacitor. It is therefore beneficial to repeat the search signal of the Reader multiple times, and stack energy on the capacitor, especially when the response signal is faint or non-existent.

FIG. 3 illustrates a handheld one LC circuit reader (FIG. 3A) employed in finding the position of a 3-Marker. The reader contains one LC circuit whose emitting frequency may be changed, for example by gradually changing the resonant frequency in steps by increasing or decreasing the capacitance in steps 38, 38b using switches 39. The reader's directional magnetic antenna transmits pulses of a given frequency to detect the position of the 3 Marker which as explained above contains 3 tubes that are not co-directional and preferentially perpendicular each to the other; they are responsive to 3 different frequencies that are known approximately in advance. They can be identified by listening for a specific response pulse by emitting sequentially the frequencies that are in the probabilities list.

The Reader starts by transmitting a powerful wide-band pulse both in frequency and angular spread; the parameters of the 3 tubes may be reduced in successive steps until a response is received. At this stage the angular width of the Reader's beam is reduced in steps while the position of the Reader is changed in steps (FIG. 3B, 31a, 32a, 33a) while looking for an increase of the intensity of the response (FIG. 3B, 31, 32, 33).

The response intensity increase may be digitally displayed on the Reader's screen and translated to sound and emitted by a speaker. When a maximal response from one of the tubes is approximately reached, the Reader repeats the same process to find the position of the second tube and then of the third tube which obviously are in the vicinity while reducing the angular width of the Reader until the response intensities 31, 32 and 33 coalesce at a certain position. Obviously the directions 31b, 32b and 33b (FIG. 3C), having error spreads, the common position of the 3-Marker also has an indeterminacy. The approximate distance along the measured direction in space (FIG. 3B, 35, Z) may be estimated according to a previously established database of "distance versus amplitude" lookup table when the Reader and a Marker are co-linear, in which case the response of the Marker is maximal. Therefore when the response is not close to maximal, the search of the Marker should concentrate on moving the Reader sideways 30 in order to find a direction that increases a larger response.

In principle an algorithm of search in 3-D may be devised that minimizes the time of search of the Marker as a function of the response at each step.

Although each Marker is unique, the number of different markers may be very large. For example, using 100 slightly different capacitors coupled to 100 different inductors, results in $10^4$ different LC circuits; as the tubes in the 2-tube Marker are orthogonal and therefore independent, the number of different markers is $10^6$. Obviously the different Markers will be of slightly different physical sizes, which may be suitable for marking lesions of different sizes. FIG. 4A illustrates a flat hand placed multiple Marker Position Identifier (MPI) 45. In the event that a body of tissue to be surgically removed has been marked at its margins with multiple markers of different unique resonant frequencies (bracket markings), there is a need to demarcate on the skin surface 44 the geographic position of the underlying embedded markers. The MPI comprises rows of multiple LC resonant Readers 46a that may be tuned to excite multiple Markers of different frequencies simultaneously by changing the values of the embedded capacitors externally and automatically (FIG. 4B, 47) when the tubes of the markers and the Readers on the MPI are at the same mutual angle. As a reader is approximately 1 $cm^2$, a 10 cm×10 cm MPI contains 100 readers with all the electronics for automatically changing the frequencies. By placing the flat MPI on the skin surface, the MPI simultaneously detects the depth and position of the multiple underlying unique frequency markers. Finding the depth of each Marker within the breast may be carried out on the basis of measuring the absolute intensities at the surface of the breast, emitted by the markers and deriving the depth from the said intensity distribution, displayed on the bottom of the MPI 50. The display 50 will simultaneously identify the relevant reader in the MPI and hence the position under the flat MPI where the relevant marker is detected. The resonant frequency of an LC circuit may be changed by changing the value of the capacitor; this can be accomplished by connecting one or more capacitors from the outside as illustrated in circuit 47 (FIG. 4B).

A speaker 48 embedded in the hand-held MPI translates all intensity related measurements when searching for tuned positions, onto sound volumes and thus indicate when the MPI approaches a direction which is in tune with a Marker.

FIG. 5A illustrates the basic structure of the "Applicator" 52 for inserting the 3 models of the Marker and the way to "anchor" a Marker in the tissue.

The one tube Marker 8 with side springy extrusions (FIG. 5A, 9 and FIG. 1E. 9) is deployed by pushing on the plunger 10 where after the small extrusions automatically deploy and grip to the tissue adjacent to the Marker.

The 2 independent tubes that form the 2-Marker (FIG. 5B, 51) are joined at their ends by an axis that traverses both tubes and a circular spring 51a that keeps the tubes mutually perpendicular. The spring allows two tubes each of approximately 0.5 mm diameter to be squeezed into a mutually narrower angle by pressing them so that they can be inserted into a larger tube with a plunger at its end. The tubes are extruded from the large carrier tube by pushing on the plunger.

The 3-Marker (FIG. 5C) containing 3 mutually perpendicular tubes 59 may also be collapsed into a slender cluster 58 and inserted into a tube 52b of 1.4 mm diameter.

When pushed out of the tube by a plunger 53b, it will spring and deploy its 3 mutually perpendicular tubes 59.

The dimensions of the tubes mentioned in these applications are for illustration purposes and any other dimensions larger or smaller than those mentioned above may be suitable for specific applications. The Applicators may have blunt ends or sharp needle ends and the markers may exit from side or end openings. FIG. 6 illustrates the structure of the "Marker tube" with the ability to "spread" relatively larger anchors 63 by turning a mechanical "lever 61" on, or retrieve said anchors turning the mechanical levers in the opposite direction 62. The tube contains a marker within it and represents an alternate method for fixing the marker in tissue than that illustrated and described in FIG. 5.

The tube outer walls have mini flaps 63 affixed at their edge to the axes 64 that runs along the wall of the tube when said axes are turned by a given angle, the flaps affixed to the axis protrude out the wall of the tube. The mechanical action of the axes that move flaps in and out of the tube walls are activated mechanically by the mechanism resident in the applicator, when implanting the Marker or retrieving it.

Figure 7:
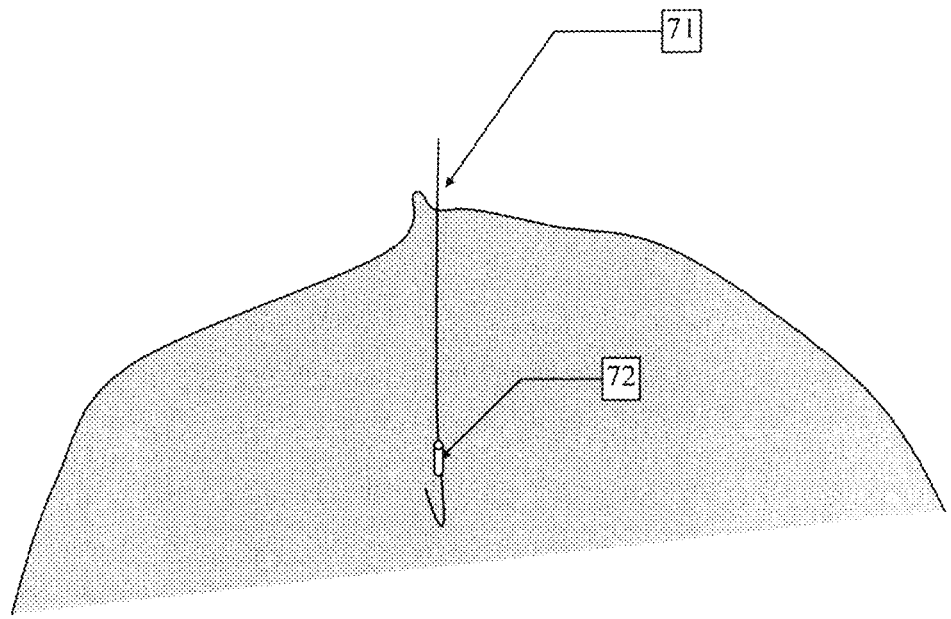
FIG. 7 illustrates a way to determine the position of a breast lesion with a localization guide-wire and a marker attached to the wire.

FIG. 7 illustrates a localization guide-wire 71 with a Marker 72 embedded above the lower end of the hook shaped guide-wire that is inserted by a lesion in the breast or any other body site requiring marking, as in the case of pulmonary lesions, where the marking of the lesion serves to locate the said lesion. The guide wire serves to guide the surgeon to the site requiring biopsy. In most instances the lesion marked by the guidewire is not palpable to the surgeon and hence excessive tissue is removed. The presence of a passive marker attached close to the end of the guidewire enables the surgeon with the aid of a Reader to accurately locate the position of the marker and henceforth that of the adjacent lesion.

Figure 8:
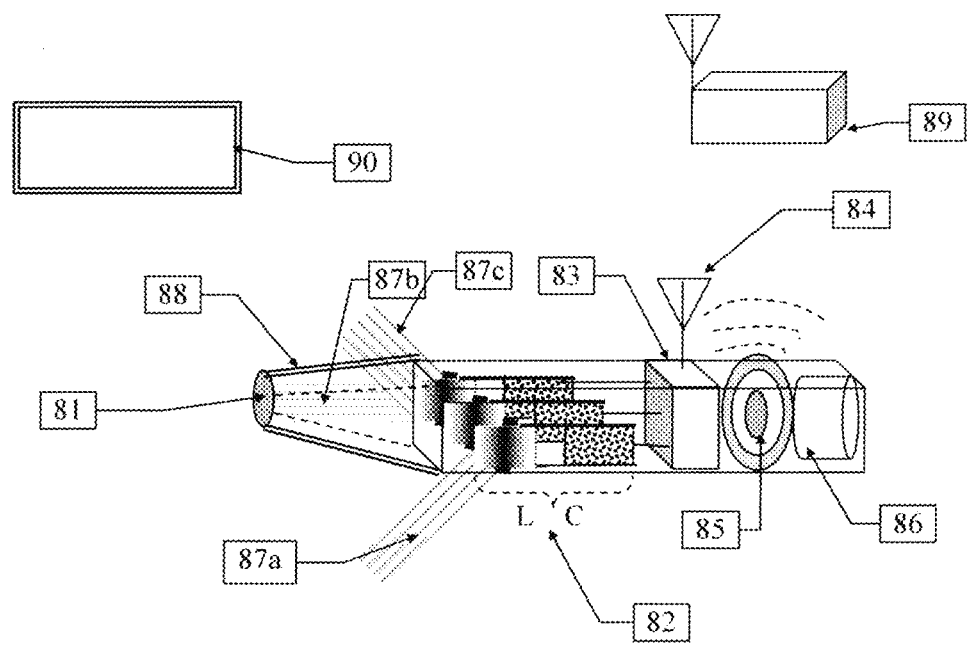
FIG. 8 illustrates a, battery operated, mini-Reader of Markers.

FIG. 8 illustrates a battery operated 86, mini-Reader of Markers, of small dimensions whose approximate cross-section at the front-end 81 that emits specific electromagnetic frequencies tuned to the searched Marker, is around 3 mm². The mini-Reader contains behind its front end 3 L-C circuits 82 tuned to different frequencies in order to be able to detect both single, 2 and 3-Markers. The specific resonant frequencies of the Markers can be changed online by connecting additional capacitors stored in a cache 83, and by activating electronic switches as illustrated in FIG. 4B (circuit 47). The elongated sides of the reader 88 are reflective; the radiation 87a, 87b, 87c exits through the end 81 which is not reflective.

The frequency of the emitted narrow electromagnetic beam is modified in a specific sequence by changing the capacitance 47 until such time that the magnitude of the response signal received from the passive Marker in said body tissue is maximal, thus determining its position in 3D. The search process, while moving the mini-Reader by hand or other means is broadcast by wireless 84 to a processor 89 that helps the manual search by oral instructions to the searching person through his earphones which also may be broadcast through a speaker 85 and displayed on a screen 90. The mini-reader may be hand operated or attached to a rigid or flexible endoscope or attached to any surgical or other instrument or operated remotely.

FIG. 9 illustrates a method to mark the borders of a biopsy specimen or surgical margin in the breast or any other body tissue and a method for being able to come back and accurately anatomically orientate the excised pathology specimen tissue and identify its previous in vivo adjacent abutting paired tissue margin. This is achieved by placing sets of paired sister markers of same frequency on abutting surgical and pathology margins intraoperatively.

Once a certain area of body tissue (FIG. 9A) is assessed as being potentially malignant, intraoperatively, the margins of the excised tissue are marked with pairs of identical Markers, (FIG. 9B, 92a, 92b; 93a, 93b; 94a, 94b and 95a, 95b) as well as its top side 95c, while the tissue is still in vivo.

The excised specimen (FIG. 9C) carrying the Markers 92b, 93b, 94b, 95b and 95c is then sent to the pathology. The margins of the pathology specimen are uniquely identified and also orientated in 3D by the pathologist using a mini reader. The pathology specimen is then stained with each unique margin as identified by its markers receiving a different color stain and regions between specific markers are noted. The pathology specimen is then sectioned with sections being corresponded to each unique margin and inter marker regions. If a region 91a between the markers 93b and 94b as orientated by the mini-Reader is found to be malignant and has reached and caused a positive pathology margin, then the surgeon returns to the surgical biopsy site (FIG. 9D) in the patient and with the use of an intraoperative reader, identifies the surgical margin between the previously inserted Markers 93a and 94a and excises further tissue in this region. He then marks the remaining body tissue (FIG. 9E) with 3 sets of Markers (96a, 96b), (97a, 97b), and (98a, 98b) and sends the additional excised tissue marked with the Markers 96b, 97b and 98b to pathology for examination, The process of excising tissue and examining it at pathology is continued until the last examination finds the margins to be clear of malignancy.

The invention claimed is:

1. A passive electronic marker device system for indicating the position of a site within the body, wherein said site includes one of a tissue lesion, a tumor, a calcification, a foreign body, a wound and a dislocation, said system comprising:

at least two electronic building block markers having first and second ends and a receptacle, each said building block marker being comprised of passive electronic components including at least one inductor and at least one capacitor in the form of a dielectric resonant antenna, and at least one resistor, and being responsive to an electromagnetic wave of a specific frequency emitted by an external electromagnetic wave source containing a transmit-receive antenna where each receptacle contains the passive electronic components, where each electronic building block marker within the system has a unique resonant frequency and in response to a specific external resonant electromagnetic wave source of frequency resonant to its own frequency, each individual electronic marker emits a unique electromagnetic wave and is thereby differentiable from other electronic building block markers within the system; and a connector which joins the first end of each electronic building block marker together to form the system wherein the system is collapsed for delivery to a target site and the at least two electronic building block markers are deployed at angles with one another so that each electronic building block marker is unique in its direction in space when deployed at the target location.

2. A multiple marker device system comprising:

at least two marker tubes, each tube containing a circuit of directional passive electronics including inductors, capacitors and resistors, each of said individual passive electronic circuits being responsive to a different resonant frequency emitted by an external electromagnetic wave source; and a connector that joins the at least two marker tubes where the multiple marker device is collapsed for delivery to a target site and the at least two marker tubes are deployed at angles with one another so that each marker tube is unique in its direction in space when deployed at the target location, wherein the multiple marker device system is implanted in a body and is configured to be located within the body by scanning the body with the external electromagnetic wave source with a narrow transmit-receive antenna at known resonant narrow band frequencies until an electromagnetic response is detected and maximized by fine-tuning positions and directions of the external source antenna; and wherein amplitudes of resonant waves emitted by an external electromagnetic source are maximized when placed along a direction of the electromagnetic waves reemitted by the responding marker tubes of the system, and wherein, the external source scans serially the different resonant frequencies of each passive electronic circuit, and wherein the external source repeats the frequency scan from different triangulation directions in space for each marker tube, wherein the intersection of mutually different directions in space, determine the position of a respective marker tubes in 3 dimensions, and wherein the depth location of the multiple marker device system is estimated according to a preset database of distance versus amplitude of the maximal response.

3. A passive electronic marker as in claim 1, further comprising a localization guide device, said localization guide device including a wire with a hook or other distal fixation configuration at its end or sides, wherein the passive electronic marker is attached to the localization guide device in the region of its distal end, wherein said guide device is placed prior to surgery at a target site in tissue of a body that is to be removed at surgery, so that the attached passive marker is positioned close to said tissue site, and wherein said localization guide device extends external to the body beyond the skin surface and acts as a mechanical guide in locating the targeted tissue site and wherein, the attached passive electronic marker is located by scanning an external electromagnetic wave source over the area of the targeted tissue site.

4. A passive electronic marker device system according to claim 1, wherein the at least two electronic building block markers is three passive electronic building block markers, and the connector joins the three passive electronic markers together to form the system.

5. A passive electronic marker device system according to claim 1, further comprising anchoring attachments attached to an outer wall of the receptacle containing passive electronic components wherein the anchoring attachments deploy automatically on extrusion of the marker system from a hollow tube applicator.

6. A passive electronic marker device system according to claim 1 wherein said receptacle may be of plastic or silicone.

7. A passive electronic marker device system according to claim 1 wherein each said receptacle has a very thin outer wall which does not impede the passage of electromagnetic waves received and emitted by its respective marker.

8. A passive electronic marker device system for indicating the position of a site within the body, wherein said site includes one of a tissue lesion, a tumor, a calcification, a foreign body, a wound and a dislocation, said system comprising:

at least two joined electronic building block markers having first and second ends and a receptacle, each said building block marker being comprised of passive electronic components including at least one inductor and at least one capacitor in the form of a dielectric resonant antenna, and at least one resistor, and being responsive to an electromagnetic wave of a specific frequency emitted by an external electromagnetic wave source containing a transmit-receive antenna where each receptacle contains the passive electronic components, where each electronic building block marker within the system has a unique resonant frequency and in response to a specific external resonant electromagnetic wave source of frequency resonant to its own frequency, each individual electronic marker emits a unique electromagnetic wave and is thereby differentiable from other electronic building block markers within the system; and a connector which joins the first end of each electronic building block marker together to form the system wherein the system is collapsed for delivery to a target site and the at least two electronic building block markers are deployed at angles with one another so that each electronic building block marker is unique in its direction in space when deployed at the target location; and a localization guide device, said localization guide device having a distal end and including a wire with a hook or other fixation configuration at the distal end, wherein the at least two joined building block markers are attached to the localization guide device in the region of its distal end or sides as a passive marker, wherein said guide device is placed prior to surgery at a target site in tissue of a body that is to be removed at surgery, so that the attached passive marker is positioned close to said tissue site, and wherein said localization guide device extends external to the body beyond the skin surface and acts as a mechanical guide in locating the targeted tissue site and wherein, the attached passive electronic marker is located by scanning an external electromagnetic wave source over the area of the targeted tissue site.

* * * * *